United States Patent
Anderson (10) Patent No.: US 10,327,695 B2
(45) Date of Patent: Jun. 25, 2019

(54) FUNCTIONAL GAIN MEASUREMENT TECHNIQUE AND REPRESENTATION

(71) Applicant: VOLCANO CORPORATION, San Diego, CA (US)

(72) Inventor: David Anderson, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 392 days.

(21) Appl. No.: 14/136,185

(22) Filed: Dec. 20, 2013

(65) Prior Publication Data

US 2014/0180035 A1    Jun. 26, 2014

Related U.S. Application Data

(60) Provisional application No. 61/745,319, filed on Dec. 21, 2012.

(51) Int. Cl.
| | |
|---|---|
| *A61B 5/026* | (2006.01) |
| *A61B 5/00* | (2006.01) |
| *A61B 5/0215* | (2006.01) |
| *A61B 5/02* | (2006.01) |
| *A61B 8/08* | (2006.01) |

(Continued)

(52) U.S. Cl.
CPC .......... *A61B 5/4848* (2013.01); *A61B 5/0066* (2013.01); *A61B 5/026* (2013.01); *A61B 5/02007* (2013.01); *A61B 5/0215* (2013.01); *A61B 8/0891* (2013.01); *A61B 8/12* (2013.01); *A61B 8/445* (2013.01); *A61B 8/461* (2013.01); *A61B 8/465* (2013.01); *A61B 8/5223* (2013.01); *A61B 5/02141* (2013.01); *A61B 8/467* (2013.01); *A61B 8/565* (2013.01)

(58) Field of Classification Search
None
See application file for complete search history.

(56) References Cited

U.S. PATENT DOCUMENTS

| 4,794,931 A | 1/1989 | Yock |
|---|---|---|
| 4,841,977 A | 6/1989 | Griffith et al. |
| | (Continued) | |

FOREIGN PATENT DOCUMENTS

| JP | 2007289541 A | 11/2007 |
|---|---|---|
| WO | WO 2012/155040 A1 | 11/2012 |
| WO | WO 2012/166332 | 12/2012 |

OTHER PUBLICATIONS

Zhang et al., "How to Analyze Change from Baseline: Absolute or Percentage Change?", D-level Essay in Statistics 2009, Jun. 10, 2009.*

(Continued)

*Primary Examiner* — Kennedy Schaetzle (57) ABSTRACT

The present invention generally relates to methods, systems, and apparatuses for determining the degree of improvement after a therapeutic procedure. The method can involve determining a baseline measurement prior to conducting a therapeutic procedure, conducting the therapeutic procedure, and determining a post-therapy measurement after conducting the therapeutic procedure. The method further involves comparing the post-therapy measurement to the baseline measurement, thereby determining the degree of improvement after conducting the therapeutic procedure.

15 Claims, 5 Drawing Sheets

(51) Int. Cl.
   *A61B 8/12* (2006.01)
   *A61B 8/00* (2006.01)
   *A61B 5/021* (2006.01)

(56) References Cited

U.S. PATENT DOCUMENTS

| | | |
|---|---|---|
| 4,917,097 A | 4/1990 | Proudian et al. |
| 4,951,677 A | 8/1990 | Crowley et al. |
| 5,000,185 A | 3/1991 | Yock |
| 5,095,911 A | 3/1992 | Pomeranz |
| 5,125,137 A | 6/1992 | Cori et al. |
| 5,135,486 A | 8/1992 | Eberle et al. |
| 5,167,233 A | 12/1992 | Eberle et al. |
| 5,176,141 A | 1/1993 | Bom et al. |
| 5,183,048 A | 2/1993 | Eberle |
| 5,240,003 A | 8/1993 | Lancee et al. |
| 5,243,988 A | 9/1993 | Sieben et al. |
| 5,313,949 A | 5/1994 | Yock |
| 5,321,501 A | 6/1994 | Swanson et al. |
| 5,353,798 A | 11/1994 | Sieben et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,453,575 A | 9/1995 | O'Donnell et al. |
| 5,921,931 A | 7/1999 | O'Donnell et al. |
| 6,106,476 A | 8/2000 | Cori et al. |
| 6,134,003 A | 10/2000 | Tearney et al. |
| 6,193,669 B1* | 2/2001 | Degany ............ A61B 5/02014 600/486 |
| 6,200,268 B1 | 3/2001 | Vince et al. |
| 6,421,164 B2 | 7/2002 | Tearney et al. |
| 6,471,656 B1* | 10/2002 | Shalman ............ A61B 5/0215 600/486 |
| 6,901,277 B2* | 5/2005 | Kaufman ............ A61B 5/411 128/922 |
| 7,074,188 B2 | 7/2006 | Nair et al. |
| 7,532,920 B1* | 5/2009 | Ainsworth ........ A61B 5/02007 600/341 |
| 7,783,337 B2 | 8/2010 | Feldman et al. |
| 7,787,127 B2 | 8/2010 | Galle et al. |
| 7,929,148 B2 | 4/2011 | Kemp |
| 7,995,210 B2 | 8/2011 | Tearney et al. |
| 7,999,938 B2 | 8/2011 | Wang |
| 8,108,030 B2 | 1/2012 | Castella et al. |
| 8,125,648 B2 | 2/2012 | Milner et al. |
| 8,187,191 B2 | 5/2012 | Hancock et al. |
| 8,277,386 B2 | 10/2012 | Ahmed et al. |
| 8,298,147 B2 | 10/2012 | Huennekens et al. |
| 8,520,918 B2* | 8/2013 | Wilson ............... A61B 5/0033 382/128 |
| 8,620,055 B2 | 12/2013 | Barratt et al. |
| 9,161,695 B2* | 10/2015 | Tsuji ................ A61B 5/02007 |
| 9,314,584 B1* | 4/2016 | Riley ................... A61M 25/00 |
| 2003/0032886 A1* | 2/2003 | Dgany ............... A61B 5/0215 600/487 |
| 2003/0100815 A1* | 5/2003 | Da Silva ............ A61B 5/02007 600/9 |
| 2003/0216621 A1* | 11/2003 | Alpert ................ A61B 5/0215 600/300 |
| 2006/0241505 A1* | 10/2006 | Ahmed .............. A61B 5/02158 600/486 |
| 2007/0088220 A1* | 4/2007 | Stahmann ........... A61B 5/02158 600/485 |
| 2007/0161897 A1 | 7/2007 | Sasaki et al. |
| 2009/0043191 A1 | 2/2009 | Castella et al. |
| 2009/0292201 A1 | 11/2009 | Kruecker |
| 2010/0220334 A1 | 9/2010 | Condit et al. |
| 2011/0152771 A1 | 6/2011 | Milner et al. |
| 2011/0178383 A1* | 7/2011 | Kassab ................ A61B 5/026 600/381 |
| 2011/0319752 A1 | 12/2011 | Steinberg et al. |
| 2012/0184859 A1 | 7/2012 | Shah et al. |
| 2012/0230565 A1 | 9/2012 | Steinberg et al. |
| 2012/0277722 A1 | 11/2012 | Gerber et al. |
| 2012/0323127 A1 | 12/2012 | Boyden et al. |
| 2013/0017274 A1* | 1/2013 | Andersen ............ A61K 33/14 424/677 |
| 2013/0030295 A1 | 1/2013 | Huennekens |
| 2013/0046190 A1* | 2/2013 | Davies ............... A61B 5/0215 600/486 |
| 2013/0066212 A1 | 3/2013 | Margolis et al. |
| 2013/0131523 A1* | 5/2013 | Suchecki ........... A61B 5/02007 600/486 |
| 2013/0303907 A1 | 11/2013 | Cori |
| 2013/0324804 A1* | 12/2013 | McKeown .......... A61B 5/0205 600/300 |
| 2014/0081244 A1* | 3/2014 | Voeller ................ A61M 25/01 604/528 |
| 2014/0180035 A1* | 6/2014 | Anderson ............ A61B 5/4848 600/301 |
| 2014/0199275 A1* | 7/2014 | Murphy ................ A61K 35/28 424/93.7 |
| 2014/0275995 A1 | 9/2014 | Sheehan |
| 2014/0275996 A1 | 9/2014 | Stigall |
| 2014/0276036 A1 | 9/2014 | Collins et al. |
| 2014/0276059 A1 | 9/2014 | Sheehan |
| 2014/0276085 A1 | 9/2014 | Miller |
| 2014/0276684 A1 | 9/2014 | Huennekens et al. |
| 2015/0087986 A1 | 3/2015 | Nair et al. |

OTHER PUBLICATIONS

L. Montgomery Smith et al., "Absolute Displacement Measurements Using Modulation of the Spectrum of White Light in a Michelson Interferometer," Applied Optics, vol. 28, No. 15, Aug. 15, 1989, pp. 3339-3342.

James B. Seward, M.D., et al, "Ultrasound Cardioscopy: Embarking on a New Journey," Mayo Clinic Proceedings, Jul. 1996, pp. 629-635, vol. 71, No. 7, Mayo Foundation for Medical Education and Research.

M. Bail, et al., "Optical Coherence Tomography with the "Spectral Radar"—Fast Optical Analysis in Volume Scatters by Short Coherence Interferometry," Optics letters vol. 21, No. 14 (1996), 1087-1089, 8 pages, Physics Institute, University of Erlangen-Nürnberg, Erlangen, Germany.

International Searching Authority/United States Patent Office, "Notification of Transmittal of the International Search Report and The Written Opinion of the International Searching Authority, or the Declaration," for PCT/US2014/023155, dated Jul. 7, 2014, 3 pages.

International Search Report and Written Opinion received in Patent Cooperation Treaty Application No. PCT/US13/076909, dated Mar. 19, 2014, 8 pages.

International Searching Authority/European Patent Office, "Communication—Supplementary European Search Report," for European Application No. 13865991.7, dated Jul. 22, 2016, 7 pages.

\* cited by examiner

| List of Runs | FFR |
|---|---|
| 03:50:19 PM | 0.75 |
| LCX Mid | |
| 03:50:39 PM | 0.88 |
| LAD Distal | |
| 03:50:53 PM | 0.75 |
| Pre RCA Mid | |
| 03:51:16 PM | 0.97 |
| Post RCA Mid | |
| Funtional Gain | 29% |

FIG. 5

| List of Runs | FFR |
|---|---|
| 09:01 AM LCX Mid | |
| ↳ 09:01 AM Baseline | 0.73 |
| ↳ 09:06 AM Post Stent | 0.82 |
| ↳ 09:09 AM IVUS/NC Balloon (22 atm) | 0.91 |
| ↳ 09:11 AM Final Confirmation | 0.91 |
| ↳ 09:11 AM Functional Gain | 26% |

FIG. 6A

| List of Runs | FFR |
|---|---|
| 09:01 AM LCX Mid | |
| ↳ 09:01 AM Baseline | 0.73 |
| ↳ 09:11 AM Final Confirmation | 0.91 |

FUNCTIONAL GAIN MEASUREMENT TECHNIQUE AND REPRESENTATION

CROSS-REFERENCE TO RELATED APPLICATIONS

This application claims the benefit of, and priority to, U.S. Provisional Application Ser. No. 61/745,319, filed Dec. 21, 2012, the contents of which are incorporated by reference herein in its entirety.

FIELD OF THE INVENTION

The present invention generally relates to methods and systems for measuring the degree of post-therapy improvement in cardiovascular procedures.

BACKGROUND

Cardiovascular disease frequently arises from the accumulation of atheromatous deposits on inner walls of vascular lumen, particularly the arterial lumen of the coronary and other vasculature, resulting in a condition known as atherosclerosis. These deposits can have widely varying properties, with some deposits being relatively soft and others being fibrous and/or calcified. In the latter case, the deposits are frequently referred to as plaque. These deposits can restrict blood flow, leading to myocardial infarction in more severe cases.

Fractional flow reserve (FFR) is a physiological measurement typically used to assess blood flow. FFR is determined by measuring the maximum myocardial flow in the presence of a stenosis (i.e., a narrowing of the blood vessel) divided by the normal maximum myocardial flow. This ratio is approximately equal to the mean hyperemic (i.e., dilated vessel) distal coronary pressure divided by the mean aortic pressure. Distal coronary pressure is usually measured with a pressure sensor mounted on the distal portion of a guidewire after administering a hyperemic agent into the blood vessel. Mean aortic pressure is measured using a variety of techniques in areas proximal of the stenosis, for example, in the aorta.

FFR provides a convenient, cost-effective way to assess the severity of coronary and peripheral lesions. FFR also provides an index of stenosis severity that allows rapid determination of whether an arterial blockage is significant enough to limit blood flow within the artery, thereby requiring treatment. The normal value of FFR is about 1.00. Values less than 0.80 are deemed significant and require treatment, which may include angioplasty and stenting.

Although FFR is useful in determining whether or not treatment is needed, current methods have yet to address the effectiveness of the provided treatment. As it is unknown whether or not the provided treatment has adequately resolved the issue, the patient may still face a long road to full recovery.

SUMMARY

The present invention provides a method for determining the effectiveness of a cardiovascular procedure by comparing a physiological measurement, such as blood flow, taken after the cardiovascular procedure, with a physiological measurement taken before the procedure, and determining the difference between the two measurements. This difference provides a measure of the treatment's effectiveness. Accordingly, methods of the invention not only allow a physician to assess a blood vessel before and after therapy, but also provide contextual information that allows the physician to determine and document the degree of post-therapy improvement, also known as functional gain.

A physician, for example, may wish to determine the effectiveness of a stent placed in a vessel to improve blood flow. In accordance with the invention, a physiological measurement such as fractional flow reserve (FFR) is taken prior to delivering the stent. This can be done using ordinary means in the art, such as using a pressure-sensing guidewire inserted into the vessel to measure blood flow. After the stent is delivered, the FFR of the vessel is again measured. In accordance with the invention, the post-stent reading is compared to the pre-stent reading and the difference is ascertained. The difference in measurements is the degree to which the stent placement has improved blood flow.

Any physiological measurement is useful for practicing the invention, including fractional flow reserve (FFR), instant free-wave ratio (IFR), coronary flow reserve (CFR), hyperemic stenosis resistance (HSR), hyperemic microvascular resistance (HMR), and index of microvascular resistance (IMR). Even intravascular ultrasound (IVUS) and optical coherence tomography (OCT) can be used, particularly if assessing vessel dilation as the physiological measurement. In preferred embodiments of the invention, however, the physiological measurement is FFR.

Methods of the invention also encompass displays that facilitate the quick assessment of pre-therapy parameters, post-therapy parameters, and the difference between the two. As provided by the invention, the displays are fully customizable to provide a selected physiological measurement at various stages of a therapeutic procedure, in addition to providing the functional gain. Displays of the invention can be provided in a variety of ways, including textual and graphical.

The invention also encompasses systems for practicing the above methods. Certain aspects of the invention are particularly amenable for computer implementation, such pre-therapy assessment, post-therapy assessment, and the comparison between the two steps. Accordingly, systems of the invention may include computers and processors for executing methods of the invention.

DETAILED DESCRIPTION

The present invention generally relates to methods and systems for determining the degree of improvement (fractional gain) in vessel flow following a cardiovascular procedure. The invention generally involves determining fractional flow reserve prior to administering a therapy, administering the therapy, determining fractional flow reserve after administering the therapy, and comparing the two values to determine fractional gain.

Although methods of the invention encompass any physiological measurement, in preferred aspects, the physiological measurement is FFR. Fractional flow reserve (FFR) is a criteria typically used to assess blood flow. Fractional flow reserve is determined by measuring maximum flow in the presence of a stenosis (i.e., a narrowing of the blood vessel) divided by normal maximum flow. This ratio is approximately equal to the mean hyperemic (i.e., dilated vessel) distal coronary pressure divided by the mean aortic pressure. Distal coronary pressure is usually measured with a pressure sensor mounted on the distal portion of a guidewire after administering a hyperemic agent into the blood vessel. Mean aortic pressure is measured using a variety of techniques in areas proximal of the stenosis, for example, in the aorta.

FFR provides a convenient, cost-effective way to assess the severity of coronary and peripheral lesions. FFR also provides an index of stenosis severity that allows rapid determination of whether a blockage is significant enough to limit blood flow within the artery, thereby requiring treatment. The normal value of FFR is about 1.00. Values less than 0.80 are deemed significant and require treatment, which may include angioplasty and stenting.

As encompassed by the invention, a baseline FFR measurement is taken prior to conducting the therapeutic procedure. The procedure is then performed, and a subsequent post-therapy FFR measurement is taken. The post-therapy measurement is compared to the baseline measurement, and the degree in improvement is ascertained. As described herein, the degree of improvement resulting from the therapy is known as functional gain. For example, the FFR of an apparently occluded blood vessel is ascertained to be 0.75. As this is below the threshold value for therapeutic intervention, the patient will receive a stent to restore flow in the vessel. After the stent procedure, FFR is again assessed in the area of interest. This time, the FFR is determined to be 0.97. Comparing the second FFR reading to the first, the patient has a functional gain of 29%. While the second FFR determination does indicate that the operation is a success, (the blood flow is now essentially at normal levels), it does not quantify the degree of success. Methods of the invention provide just that, the ability to determine and document the degree of improvement after a therapeutic procedure has been performed. Accordingly, methods of the invention provide highly practical tools to monitor a patient's progress after therapeutic intervention.

Determination of FFR typically involves the insertion of a pressure sensing guidewire into a blood vessel and measuring pressure inside the vessel with the device. The actual parameters and calculations for determining FFR are well known in the art and are described above.

In practice, measuring pressure inside the vessel may also involve injecting a local anesthetic into the skin to numb the area of the patient prior to surgery. A puncture is then made with a needle in either the femoral artery of the groin or the radial artery in the wrist before the provided guidewire is inserted into the arterial puncture. Once positioned, the guidewire may then be used to measure pressure in the vessel, and subsequently FFR.

In a typical procedure, the guidewire may be advanced to a location on the distal side of the stenosis. The pressure may then be measured at a first flow state. Then, the flow rate may be significantly increased, for example by the use of drugs such as adenosine, and the pressure measured in this second, hyperemic, flow state. The pressure and flow relationships at these two flow states are then compared to assess the severity of the stenosis and provide improved guidance for any coronary interventions. As explained above, FFR is a comparison of the pressure within a vessel at positions prior to the stenosis and after the stenosis. The level of FFR determines the significance of the stenosis, which allows physicians to more accurately identify clinically relevant stenosis. For example, an FFR measurement above 0.80 indicates normal coronary blood flow and a non-significant stenosis. A measurement below 0.80 indicates the necessity of therapeutic intervention Any medical device can be used in conjunction with the provided methods for taking physiological measurements (e.g., FFR), before and after a therapeutic procedure. In certain embodiments, the device is configured for insertion into a bodily lumen, such as a guidewire or catheter. In other embodiments, the medical device is a pressure-sensing guidewire or catheter. In additional embodiments, the medical device is flow-sensing guidewire or catheter. In further embodiments, the encompassed guidewire or catheter has both flow and pressure measuring capabilities.

Figure 1:
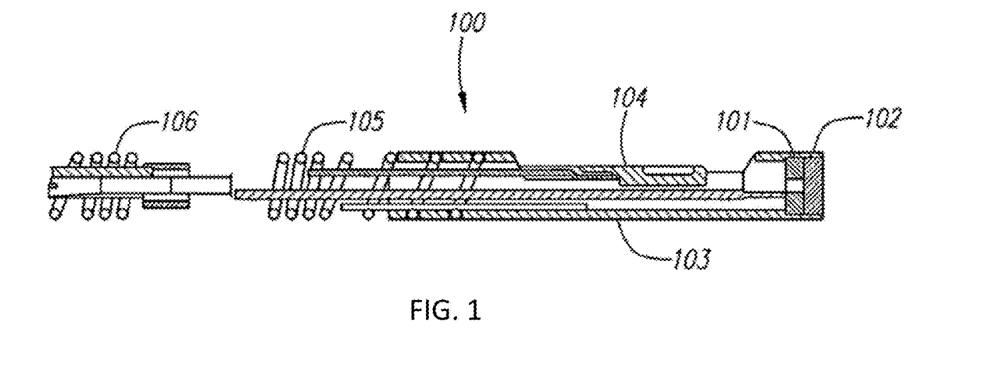
FIG. 1 illustrates a combination guidewire with pressure and flow measuring capabilities for use in practicing methods of the invention.
Figure 2:
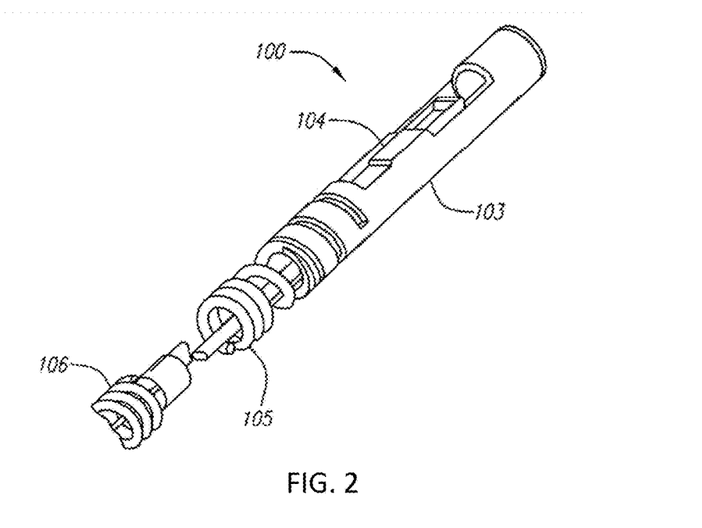
FIG. 2 illustrates an alternative view of the combination guidewire of FIG. 1.

An exemplary guidewire for practicing methods of the invention is depicted in FIGS. 1 and 2. The exemplary guidewire shown has both pressure and flow measuring capabilities. A guidewire with both a pressure sensor and a flow sensor provides a desirable environment in which to calculate fractional flow reserve (FFR) using pressure readings, and coronary flow reserve (CFR) using flow readings. CFR, like FFR, is another exemplary physiological measurement that can be used in practicing methods of the invention. Moreover, the invention is equally applicable to any type of physiological measurement, including fractional flow reserve (FFR), instant free-wave ratio (IFR), coronary flow reserve (CFR), hyperemic stenosis resistance (HSR), hyperemic microvascular resistance (HMR), and index of microvascular resistance (IMR). Methods of the invention may also be applied to intravascular imaging (IVUS) or optical coherence tomography (OCT), particularly if these physiological measurements were used to determine compare the difference in luminal area. Any of these physiological measurements can be taken prior to therapeutic invention, subsequent to therapeutic invention, and have the two values compared to determine functional gain.

Turning to FIGS. 1 and 2, a combination sensor tip 100 for practicing the invention is illustrated. The combination sensor tip 100 includes a flow sensor 101, for example an ultrasound transducer, a Doppler flow sensor or any other suitable flow sensor, disposed at or in close proximity to the distal end 102 of the combination sensor tip 100. The ultrasound transducer 101 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 101, and the conductors may extend interiorly to the proximal extremity of a guide wire.

The combination sensor tip 100 also includes a pressure sensor 104 also disposed at or in close proximity to the distal end 102 of the combination sensor tip 100. The pressure sensor 104 may be of the type described in U.S. Pat. No. 6,106,476, which is fully incorporated herein by reference. For example, the pressure sensor 104 may be comprised of a crystal semiconductor material having a recess therein and forming a diaphragm bordered by a rim. A reinforcing member may be bonded to the crystal to reinforce the rim of the crystal, and may have a cavity therein underlying the diaphragm and exposed to the diaphragm. A resistor having opposite ends may be carried by the crystal and may have a portion thereof overlying a portion of the diaphragm. Leads may be connected to opposite ends of the resistor and extend proximally within the guide wire. Additional details of suitable pressure sensors that may be used as the pressure sensor 104 are described in U.S. Pat. Nos. 6,106,476. 6,106,476 also describes suitable methods for mounting the pressure sensor 104 within the combination sensor tip 100. In one embodiment, the pressure sensor 104 is oriented in a cantilevered position within a sensor housing 103. For example, the sensor housing 103 preferably includes a lumen surrounded by housing walls. When in a cantilevered position, the pressure sensor 104 projects into the lumen of the sensor housing 103 without contacting the walls of the sensor housing 103.

As depicted in FIGS. 1 and 2, the combination sensor tip 100 incorporates a sensor housing 103 designed to enclose both the ultrasound transducer 101 and the pressure sensor 104. One advantage of the sensor housing 103 is that because the sensor housing 103 encloses both the ultrasound transducer 101 and the pressure sensor 104, the need for two separate housings, i.e., one for an ultrasound transducer and one for a pressure sensor, is eliminated. Accordingly, the use of a common sensor housing 103 for the ultrasound transducer 101 and the pressure sensor 104 makes the combination sensor tip 100 easier to manufacture than current designs. Further detail on exemplary catheters for use in practicing the invention is described in U.S. Pat. No. 8,277,386, incorporated herein by reference.

Methods of the invention also encompass displaying the obtained information, including the pre-therapy FFR, post-therapy-FFR, and functional gain in a format that is convenient and easily understandable to the physician. This may encompass displaying such information visually on a monitor or on a printed medium. The information may also be presented textually (using letters and/or numbers), graphically (e.g., bar graphs, pie charts, etc.), or a combination of the two. The display of such information is facilitated by systems of the invention, described in more detail below.

Figure 3:
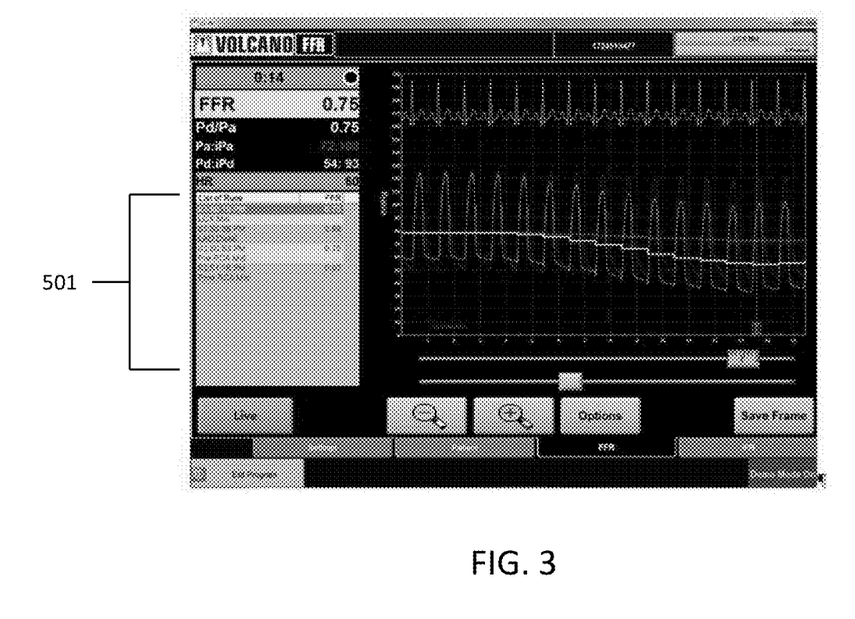
FIG. 3 is a graphical display of a Fractional Flow Reserve (FFR) determination.
Figure 4:
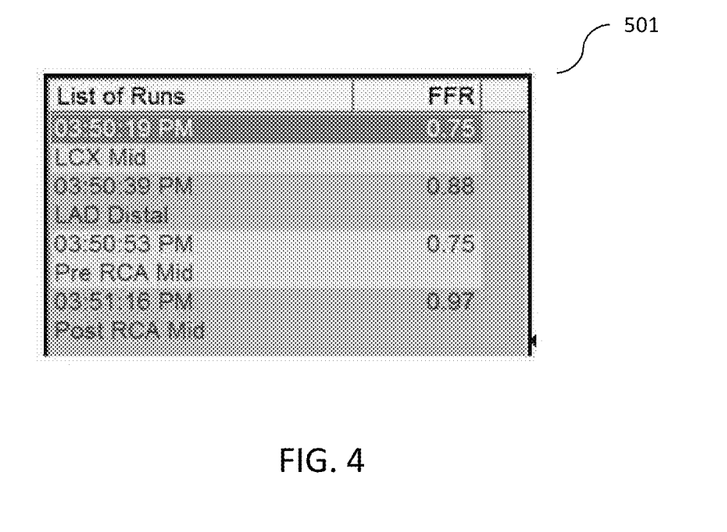
FIG. 4 is an enlarged view of a sub-window provided in the graphical display of FIG. 3.

A visual display in accordance with the invention is provided in FIG. 3, which depicts FFR data in a visual format for display on a monitor. Sub-window 501 provides data from FFR measurements conducted before and after therapeutic intervention. An enlarged view of data presented in sub-window 501 is presented in FIG. 4. As presented, sub-window 501 provides pre-therapy FFR data (Pre-RCA Mid 0.75) and post-therapy FFR data (Post-RCA Mid 0.97). Although the therapeutic procedure performed here involved a stent delivery, the invention encompasses any therapeutic procedure, particular cardiovascular procedures. Additional exemplary therapeutic procedures include, without limitation, angioplasties, ablations, and excisions. Any therapeutic procedure may be performed and its effectiveness assessed using the methods provided herein.

Figure 5:
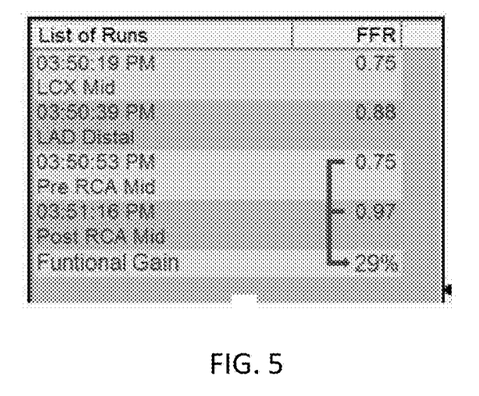
FIG. 5 is another graphical display of information determined by exemplary methods of the invention.

FIG. 5 shows another display based on the same data set. This time, however, the display provides the degree of improvement, i.e., the functional gain, after placing the stent. As shown, the post-therapy FFR (0.97) is compared to the pre-therapy FFR (0.75) to arrive at an improvement in FFR (and accordingly, vessel flow) of 29%. The pre- and post-therapy physiological measurements may be compared in any number of ways to arrive at the functional gain. In this example, functional gain is represented as a percentage difference, however, the pre-therapy measurement could have just as been easily been subtracted from the post-therapy measurement.

Figure 6A:
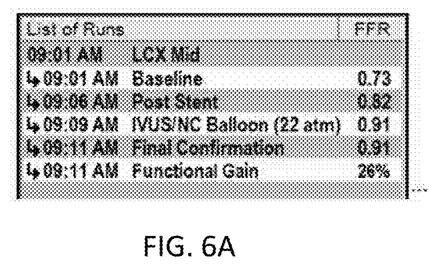
FIG. 6A and 6B are graphical displays of information determined by exemplary methods of the invention.
Figure 6B:
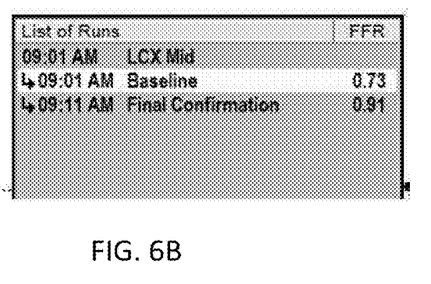

It is also encompassed that the display of information is highly customizable. As shown in FIG. 6A, physiological measurements can be taken at several points, any of which can be used to determine functional gain. In the example of FIG. 6A, a baseline FFR was taken prior to any therapeutic intervention (0.73). FFR was again measured after placing a stent (0.82). Further treatment involved post-stent dilatation with a high pressure balloon and FFR was again assessed (0.91). FFR was determined again as a final confirmation (0.91). The provided customizable displays allow for collapsing certain information, as shown in FIG. 6B. In this case, functional gain can be assessed using the baseline value and the final confirmation value to determine the degree of improvement after the two medical procedures.

As previously described herein, methods of the invention may also be applied to intravascular imaging (IVUS) or optical coherence tomography (OCT), particularly if physiological measurements, including FFR, IFR, CFR, HSR, HMR, and IMR, are used to determine or compare the difference in luminal area.

In some embodiments, the methods of the invention include use of an IVUS imaging assembly. The imaging assembly can be a phased-array IVUS imaging assembly, a pull-back type IVUS imaging assembly, including rotational IVUS imaging assemblies, or an IVUS imaging assembly that uses photoacoustic materials to produce diagnostic ultrasound and/or receive reflected ultrasound for diagnostics. IVUS imaging assemblies and processing of IVUS data are described for example in Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373,845, Seward et al., Mayo Clinic Proceedings 71(7):629-635 (1996), Packer et al., Cardiostim Conference 833 (1994), "Ultrasound Cardioscopy," Eur. J.C.P.E. 4(2):193 (June 1994), Eberle et al., U.S. Pat. No. 5,453,575, Eberle et al., U.S. Pat. No. 5,368,037, Eberle et at., U.S. Pat. No. 5,183,048, Eberle et al., U.S. Pat. No. 5,167,233, Eberle et at., U.S. Pat. No. 4,917,097, Eberle et at., U.S. Pat. No. 5,135,486, and other references well known in the art relating to intraluminal ultrasound devices and modalities. All of these references are incorporated by reference herein in their entirety.

IVUS imaging is widely used in interventional cardiology as a diagnostic tool for assessing a diseased vessel, such as an artery, within the human body to determine the need for treatment, to guide an intervention, and/or to assess its effectiveness. An IVUS device including one or more ultrasound transducers is introduced into the vessel and guided to the area to be imaged. The transducers emit and then receive backscattered ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a 360 degree cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer. Suitable rotational IVUS catheters include, for example the REVOLUTION 45 MHz catheter (offered by the Volcano Corporation).

In contrast, solid-state IVUS devices carry a transducer complex that includes an array of ultrasound transducers distributed around the circumference of the device connected to a set of transducer controllers. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. The same transducer elements can be used to acquire different types of intravascular data. The different types of intravascular data are acquired based on different manners of operation of the transducer elements. The solid-state scanner can be wired directly to the imaging system with a simple electrical cable and a standard detachable electrical connector.

The transducer subassembly can include either a single transducer or an array. The transducer elements can be used to acquire different types of intravascular data, such as flow data, motion data and structural image data. For example, the different types of intravascular data are acquired based on different manners of operation of the transducer elements. For example, in a gray-scale imaging mode, the transducer elements transmit in a certain sequence one gray-scale IVUS image. Methods for constructing IVUS images are well-known in the art, and are described, for example in Hancock et al. (U.S. Pat. No. 8,187,191), Nair et al. (U.S. Pat. No. 7,074,188), and Vince et al. (U.S. Pat. No. 6,200,268), the content of each of which is incorporated by reference herein in its entirety. In flow imaging mode, the transducer elements are operated in a different way to collect the information on the motion or flow. This process enables one image (or frame) of flow data to be acquired. The particular methods and processes for acquiring different types of intravascular data, including operation of the transducer elements in the different modes (e.g., gray-scale imaging mode, flow imaging mode, etc.) consistent with the present invention are further described in U.S. patent application Ser. No. 14/037,683, the content of which is incorporated by reference herein in its entirety.

The acquisition of each flow frame of data is interlaced with an IVUS gray scale frame of data. Operating an IVUS catheter to acquire flow data and constructing images of that data is further described in O'Donnell et al. (U.S. Pat. No. 5,921,931), U.S. Provisional Patent Application No. 61/587,834, and U.S. Provisional Patent Application No. 61/646,080, the content of each of which is incorporated by reference herein its entirety. Commercially available fluid flow display software for operating an IVUS catheter in flow mode and displaying flow data is CHROMAFLO (IVUS fluid flow display software offered by the Volcano Corporation). Suitable phased array imaging catheters include Volcano Corporation's EAGLE EYE Platinum Catheter, EAGLE EYE Platinum Short-Tip Catheter, and EAGLE-EYE Gold Catheter.

Accordingly, as encompassed by the invention, baseline IVUS image data of the vessel, including flow data, may be captured by an IVUS catheter having flow data capturing capabilities, such as the phased-array catheters described above. The baseline image data is captured prior to conducting the therapeutic procedure. The procedure is then performed, and subsequent post-therapy IVUS image data, including flow data, of the vessel is captured. The post-therapy IVUS image data is then compared to the baseline IVUS image data, upon which the degree in improvement is ascertained according to methods previously described herein.

In other embodiments, methods of the present invention include use of OCT imaging. OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

In OCT, a light source delivers a beam of light to an imaging device to image target tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Aspects of the invention may obtain imaging data from an OCT system, including OCT systems that operate in either the time domain or frequency (high definition) domain. Basic differences between time-domain OCT and frequency-domain OCT is that in time-domain OCT, the scanning mechanism is a movable minor, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference minor, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. Nos. 7,999, 938; 7,995,210; and 7,787,127 and differential beam path systems are described in U.S. Pat. Nos. 7,783,337; 6,134, 003; and 6,421,164, the contents of each of which are incorporated by reference herein in its entirety.

In some embodiments, methods of the present invention may capture baseline OCT image data of the vessel, wherein the baseline image data may be captured prior to conducting the therapeutic procedure. The procedure is then performed, and subsequent post-therapy OCT image data of the vessel is captured. The post-therapy image data is then compared to the baseline image data, upon which the degree in improvement is ascertained according to methods previously described herein.

In certain embodiments, angiogram image data may also be obtained simultaneously with the imaging data (IVUS or OCT). In such embodiments, the IVUS or OCT imaging devices may include one or more radiopaque labels that allow for co-locating image data with certain positions on a vasculature map generated by an angiogram. Co-registration generally refers to any method of re-aligning images, and in particular aligning or overlaying images from different modalities. Co-registration is often used to overlay structural and functional images as well as link functional scans to anatomical scans. Any number of modalities is useful for co-registration. Furthermore, modalities suitable for co-registration include functional measurement parameters, including, but not limited to, vessel flow, vessel pressure, FFR, iFR, CFR, etc. Details regarding image co-registration can be found in, for example, in U.S. Pat. No. 8,298,147; U.S. Patent Publication. Nos. 2012/0230565; 2011/0319752; and 2013/0030295; and U.S. Patent Appln. Nos. 13/388,932; 61/776,863, 61/776,858; 61/777,155; 61/777, 860; 61/779,610; and 61/792,230, each of which is incorporated herein by reference in its entirety.

As noted above, it is contemplated that certain aspects of the invention are particularly amenable for implementation on computer-based systems. Accordingly, the invention also provides systems for practicing the above methods. The system may comprise a processor and a computer readable storage medium instructions that when executed, cause the computer to determine a baseline measurement prior to conducting a therapeutic procedure and determine a post-therapy measurement after conducting the therapeutic procedure. The instructions may also cause the computer to compare the post-therapy measurement to the baseline measurement, thereby determining the degree of post-therapy improvement after conducting the therapeutic procedure. In further aspects, the system displays the various measurements and comparisons in a form that is ready understandable to the operator, for example, in a textual or graphical format.

Figure 7:
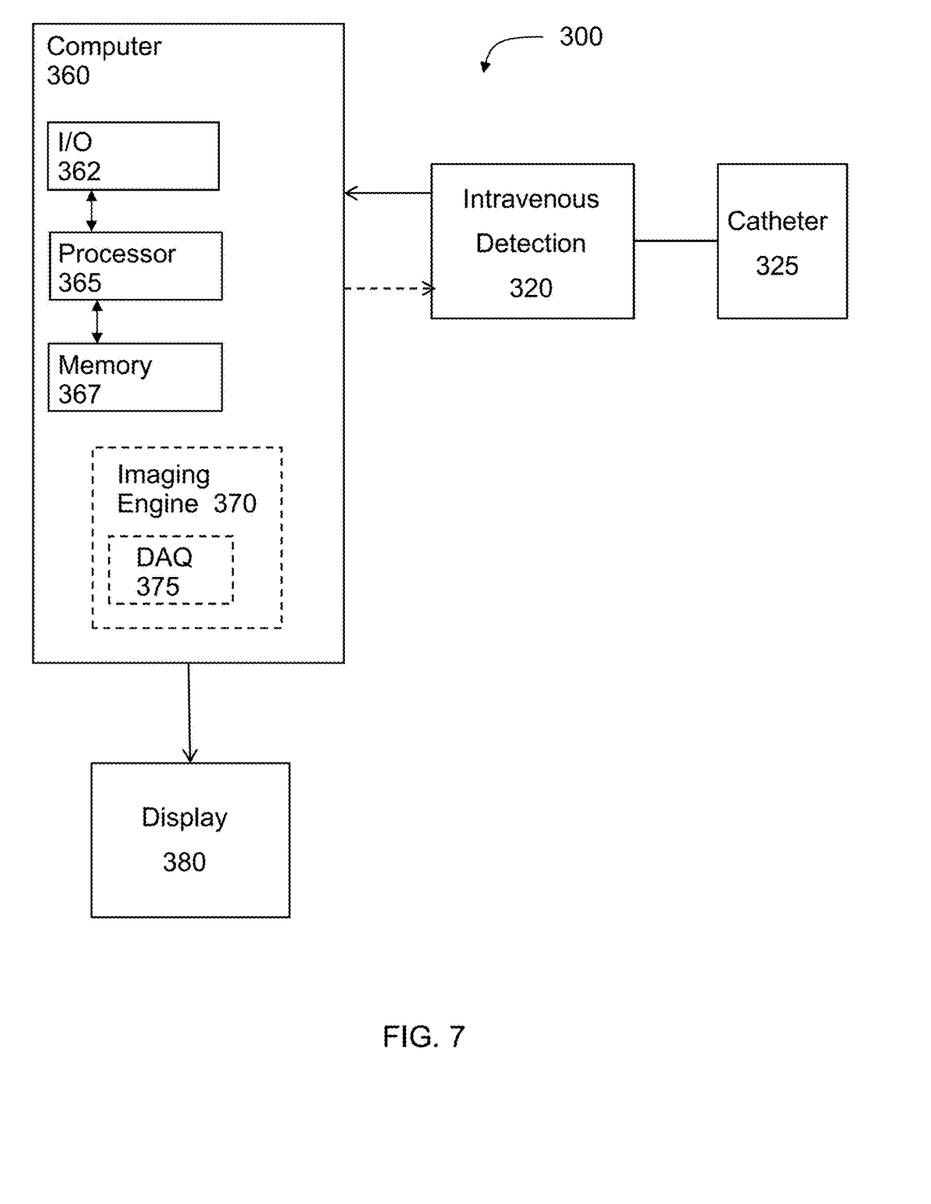
FIG. 7 is a block diagram of an exemplary system for determining the rotational orientation of an imaging device.

A system of the invention may be implemented in a number of formats. An embodiment of a system 300 of the invention is shown in FIG. 7. The core of the system 300 is a computer 360 or other computational arrangement comprising a processor 365 and memory 367. The memory has instructions which when executed cause the processor to determine a baseline measurement prior to conducting a therapeutic procedure and determine a post-therapy measurement after conducting the therapeutic procedure. The instructions may also cause the computer to compare the post-therapy measurement to the baseline measurement, thereby determining the degree of post-therapy improvement after conducting the therapeutic procedure. The physiological measurement data of vasculature will typically originate from an intravascular measurement device 320, which is in electronic and/or mechanical communication with a sensing catheter 325. Having collected the baseline measurement and post-therapy measurement, the processor then processes and outputs the results. The results are typically output to a display 380 to be viewed by a physician or technician. In some embodiments the display will include pre-therapy data, post-therapy data, and functional gain data that correlate the pre- and post-therapy data, as shown in FIG. 5. In certain embodiments, the displayed information is presented in a textual format as shown in FIG. 5. In other embodiments, the information may be presented in graphical format, like a pie chart or bar graph.

Systems of the invention may rely on the operator instructing the computer which measurement is the baseline measurement and which is the post-procedure measurement. Based on those instructions, the computer would then determine the functional gain achieved as a result of the procedure. It is contemplated that computers may one day be able to determine which measurements are which without operator intervention. For example, the software run by the computer may use co-registration to know that certain measurements were made at the same spot and are thus related. It is also contemplated that systems of the invention may integrate with the case log and determine that a measurement has been made in the same location immediately after stent deployment, and therefore assign a post-therapy designation to the measurement.

In advanced embodiments, system 300 may comprise an imaging engine 370 which has advanced image processing features, such as image tagging, that allow the system 300 to more efficiently process and display intravascular and angiographic images. The imaging engine 370 may automatically highlight or otherwise denote areas of interest in the vasculature. The imaging engine 370 may also produce 3D renderings or other visual representations of the physiological measurements. In some embodiments, the imaging engine 370 may additionally include data acquisition functionalities (DAQ) 375, which allow the imaging engine 370 to receive the physiological measurement data directly from the catheter 325 or collector 347 to be processed into images for display.

Other advanced embodiments use the I/O functionalities 362 of computer 360 to control the intravascular measurement 320. In these embodiments, computer 360 may cause the imaging assembly of catheter 325 to travel to a specific location, e.g., if the catheter 325 is a pull-back type. While not shown here, it is also possible that computer 360 may control a manipulator, e.g., a robotic manipulator, connected to catheter 325 to improve the placement of the catheter 325.

Figure 8:
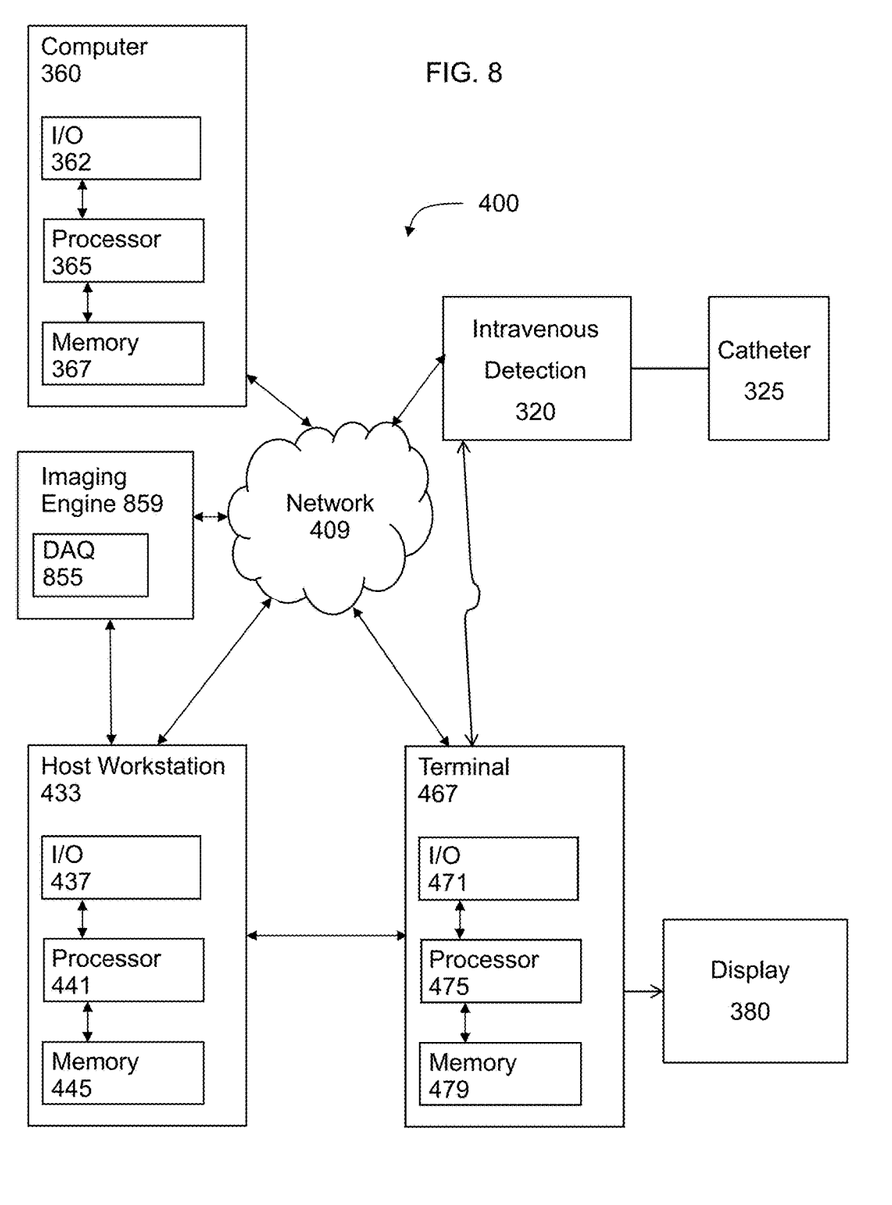
FIG. 8 is a block diagram of an exemplary networked system for determining the rotational orientation of an imaging device.

A system 400 of the invention may also be implemented across a number of independent platforms which communicate via a network 409, as shown in FIG. 8. Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

As shown in FIG. 8, the intravascular detecting system 320 facilitate obtaining the data, however the actual implementation of the steps can be performed by multiple processors working in communication via the network 409, for example a local area network, a wireless network, or the internet. The components of system 400 may also be physically separated. For example, terminal 467 and display 380 may not be geographically located with the intravascular detection system 320.

As shown in FIG. 8, imaging engine 859 communicates with host workstation 433 as well as optionally server 413 over network 409. In some embodiments, an operator uses host workstation 433, computer 449, or terminal 467 to control system 400 or to receive images. An image may be displayed using an I/O 454, 437, or 471, which may include a monitor. Any I/O may include a monitor, keyboard, mouse, or touch screen to communicate with any of processor 421, 459, 441, or 475, for example, to cause data to be stored in any tangible, nontransitory memory 463, 445, 479, or 429. Server 413 generally includes an interface module 425 to communicate over network 409 or write data to data file 417. Input from a user is received by a processor in an electronic device such as, for example, host workstation 433, server 413, or computer 449. In certain embodiments, host workstation 433 and imaging engine 855 are included in a bedside console unit to operate system 400.

In some embodiments, the system may render three dimensional imaging of the vasculature or the intravascular images. An electronic apparatus within the system (e.g., PC, dedicated hardware, or firmware) such as the host workstation 433 stores the three dimensional image in a tangible, non-transitory memory and renders an image of the 3D tissues on the display 380. In some embodiments, the 3D images will be coded for faster viewing. In certain embodiments, systems of the invention render a GUI with elements or controls to allow an operator to interact with three dimensional data set as a three dimensional view. For example, an operator may cause a video affect to be viewed in, for example, a tomographic view, creating a visual effect of travelling through a lumen of vessel (i.e., a dynamic progress view). In other embodiments an operator may select points from within one of the images or the three dimensional data set by choosing start and stop points while a dynamic progress view is displayed in display. In other embodiments, a user may cause an imaging catheter to be relocated to a new position in the body by interacting with the image. In some embodiments, a user interacts with a visual interface and puts in parameters or makes a selection. Input from a user (e.g., parameters or a selection) are received by a processor in an electronic device such as, for example, host workstation 433, server 413, or computer 449. The selection can be rendered into a visible display. In some embodiments, an operator uses host workstation 433, computer 449, or terminal 467 to control system 400 or to receive images. An image may be displayed using an I/O 454, 437, or 471, which may include a monitor. Any I/O may include a keyboard, mouse or touch screen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417. Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections). In certain embodiments, host workstation 433 and imaging engine 855 are included in a bedside console unit to operate system 400.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, NAND-based flash memory, solid state drive (SSD), and other flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell networks (3G, 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl ), and it can be deployed in any form, including as a stand-alone program or as a module, component, subroutine, or other unit suitable for use in a computing environment. Systems and methods of the invention can include programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment) into patterns of magnetization by read/write heads, the patterns then representing new collocations of information desired by, and useful to, the user. In some embodiments, writing involves a physical transformation of material in tangible, non-transitory computer readable media with certain properties so that optical read/write devices can then read the new and useful collocation of information (e.g., burning a CD-ROM). In some embodiments, writing a file includes using flash memory such as NAND flash memory and storing information in an array of memory cells include floating-gate transistors. Methods of writing a file are well-known in the art and, for example, can be invoked automatically by a program or by a save command from software or a write command from a programming language.

In certain embodiments, display 380 is rendered within a computer operating system environment, such as Windows, Mac OS, or Linux or within a display or GUI of a specialized system. Display 380 can include any standard controls associated with a display (e.g., within a windowing environment) including minimize and close buttons, scroll bars, menus, and window resizing controls. Elements of display 380 can be provided by an operating system, windows environment, application programming interface (API), web browser, program, or combination thereof (for example, in some embodiments a computer includes an operating system in which an independent program such as a web browser runs and the independent program supplies one or more of an API to render elements of a GUI). Display 380 can further include any controls or information related to viewing images (e.g., zoom, color controls, brightness/contrast) or handling files comprising three-dimensional image data (e.g., open, save, close, select, cut, delete, etc.). Further, display 380 can include controls (e.g., buttons, sliders, tabs, switches) related to operating a three dimensional image capture system (e.g., go, stop, pause, power up, power down).

In certain embodiments, display 380 includes controls related to three dimensional imaging systems that are operable with different imaging modalities. For example, display 380 may include start, stop, zoom, save, etc., buttons, and be rendered by a computer program that interoperates with IVUS, OCT, or angiogram modalities. Thus display 380 can display an image derived from a three-dimensional data set with or without regard to the imaging mode of the system.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for determining improvement of a physiological property after a therapeutic procedure, the method comprising:

obtaining, prior to conducting the therapeutic procedure, first pressure measurements using a pressure sensor disposed at a distal portion of an intravascular pressure-sensing guidewire positioned within a vessel of a patient;

determining, at a computer in communication with the intravascular pressure-sensing guidewire and prior to conducting the therapeutic procedure, a baseline quantity of a physiological property associated with the vessel, wherein the physiological property comprises a pressure ratio calculated using the first pressure measurements;

conducting the therapeutic procedure to treat the vessel;

obtaining, after conducting the therapeutic procedure, second pressure measurements using the pressure sensor of the intravascular pressure-sensing guidewire positioned within the vessel;

determining, at the computer and after conducting the therapeutic procedure, a post-therapy quantity of the physiological property based on the second pressure measurements;

comparing, at the computer, the post-therapy quantity to the baseline quantity;

calculating, at the computer based on the comparison of the post-therapy quantity to the baseline quantity, a functional gain of the physiological property as a result of the therapeutic procedure; and outputting, to a display in communication with the computer, a visual representation of the comparing, wherein the visual representation of the comparing comprises displaying:
- a numerical value associated with the functional gain;
- at least one of a numerical value associated with the baseline quantity or a numerical value associated with the post-therapy quantity; and
- a visual rendering of the vessel that includes an indication of at least one of the baseline quantity or the post-therapy quantity at a corresponding location of the visual rendering of the vessel.

2. The method of claim 1, wherein the determining the baseline quantity and post-therapy quantity comprises measuring an amount of flow and/or pressure in the vessel.

3. The method of claim 2, wherein the vessel is a blood vessel.

4. The method of claim 1, wherein physiological property is selected from fractional flow reserve, instant free-wave ratio, hyperemic stenosis resistance, hyperemic microvascular resistance, index of microvascular resistance, or a combination thereof.

5. The method of claim 1, wherein the therapeutic procedure comprises a cardiovascular procedure.

6. The method of claim 5, wherein the cardiovascular procedure is selected from an angioplasty, a stent placement, an ablation, or a combination thereof.

7. The method of claim 1, further comprising inserting the intravascular pressure-sensing guidewire into the vessel.

8. The method of claim 7, further comprising guiding the intravascular pressure-sensing guidewire to a stenosis within the vessel, wherein the first pressure measurements are obtained distal to the stenosis.

9. An intravascular system, comprising:
an intravascular pressure-sensing guidewire configured for positioning within a vessel of a patient and comprising a pressure sensor disposed at a distal portion of the intravascular pressure-sensing guidewire and configured to obtain pressure measurements associated with the vessel;

a display; and a computer in communication with the intravascular pressure-sensing guidewire and the display, wherein the computer is operable to:
- determine, prior to conducting a therapeutic procedure, a baseline quantity of a physiological property associated with the vessel, wherein the physiological property comprises a pressure ratio calculated using pressure measurements obtained by the intravascular pressure-sensing guidewire while positioned within the vessel;
- determine, after conducting the therapeutic procedure, a post-therapy quantity of the physiological property based on the pressure measurements obtained by the intravascular pressure-sensing guidewire positioned within the vessel;
- compare the post-therapy quantity to the baseline quantity;
- calculate, based on the comparison of the post-therapy quantity to the baseline quantity, a functional gain of the physiological property as a result of the therapeutic procedure; and
- output, to the display, a visual representation of the comparison, wherein the visual representation of the comparison comprises displaying:
  - a numerical value associated with the functional gain;
  - at least one of a numerical value associated with the baseline quantity or a numerical value associated with the post-therapy quantity; and
  - a visual rendering of the vessel that includes an indication of at least one of the baseline quantity or the post-therapy quantity at a corresponding location of the visual rendering of the vessel.

10. The system of claim 9, wherein the baseline measurement and the post-therapy measurement comprise at least one of a flow measurement or a pressure measurement.

11. The system of claim 9, wherein the vessel comprises a blood vessel.

12. The system of claim 9, wherein the baseline measurement and the post-therapy measurement comprise at least one of fractional flow reserve, instant free-wave ratio, hyperemic stenosis resistance, hyperemic microvascular resistance, or index of microvascular resistance.

13. The system of claim 9, wherein the visual representation comprises at least one of a graphical representation or a textual representation.

14. The system of claim 13, wherein the numerical value comprises at least one of a difference or a percentage change, between the post-therapy measurement and the baseline measurement.

15. The system of claim 9, wherein the computer is further operable to:
compare a further post-therapy quantity to at least one of the baseline quantity or the post-therapy quantity; and
wherein the visual representation of the comparison comprises a numerical value associated with the further post-therapy quantity in a manner that indicates a functional improvement in the physiological property as a result of a further therapeutic procedure.

* * * * *